United States Patent [19]

Ancel et al.

[11] Patent Number: 5,637,779
[45] Date of Patent: Jun. 10, 1997

[54] PROCESS FOR THE PREPARATION OF VITAMIN A AND NEW INTERMEDIATES

[75] Inventors: Jean-Erick Ancel; Hugues Bienayme, both of Lyons, France

[73] Assignee: Rhone-Poulenc Nutrition Animale, Antony, France

[21] Appl. No.: 383,209

[22] Filed: Feb. 3, 1995

[30] Foreign Application Priority Data

Feb. 4, 1994 [FR] France ............................ 94 01260

[51] Int. Cl.$^6$ ............................................. C07C 35/18
[52] U.S. Cl. ................................. 568/824; 568/447
[58] Field of Search ................................ 568/824, 447

[56] References Cited

U.S. PATENT DOCUMENTS

| | | | |
|---|---|---|---|
| 2,683,746 | 7/1954 | Benton, Jr. et al. | 260/598 |
| 2,811,561 | 10/1957 | Fletcher | 260/598 |
| 3,949,006 | 4/1976 | Oroshnik | 260/617 A |
| 4,035,425 | 7/1977 | Oroshnik | 260/617 A |
| 4,092,366 | 5/1978 | Oroshnik | 568/824 |
| 4,120,868 | 10/1978 | Jaedicke et al. | 260/340.7 |
| 4,147,886 | 4/1979 | Wiederkehr | 568/824 |
| 4,760,193 | 7/1988 | Duhamel et al. | 568/459 |
| 4,788,344 | 11/1988 | Duhamel et al. | 568/614 |
| 4,906,795 | 3/1990 | Grosselin et al. | 568/824 |
| 5,206,442 | 4/1993 | Mackenroth et al. | 568/447 |
| 5,243,097 | 9/1993 | Mignani et al. | 568/873 |

FOREIGN PATENT DOCUMENTS 2028330  3/1980  United Kingdom .

*Primary Examiner*—Gary L. Geist
*Assistant Examiner*—Barbara S. Frazier
*Attorney, Agent, or Firm*—Finnegan, Henderson, Farabow, Garrett & Dunner, L.L.P.

[57] ABSTRACT

A process for the preparation of vitamin A which comprises condensing ethynyl-β-ionol with the acetal of a $C_5$ allylic halide in the presence of a catalytic amount of a copper-based catalyst and a base; hydrogenating the condensed compound; eliminating the hydroxyl functional group to obtain retinal; and correcting the retinal obtained.

14 Claims, No Drawings

PROCESS FOR THE PREPARATION OF VITAMIN A AND NEW INTERMEDIATES

The present invention is directed to a new process for the preparation of vitamin A and new intermediates obtained during the various steps of this process. The present invention is more particularly directed to a process for the preparation of vitamin A bit condensation of ethynyl-β-ionol with a $C_5$ unit carrying an allylic chloride.

It is known to prepare vitamin A by a related process such as the process described in U.S. Pat. No. 4,035,425, which describes the condensation of ethynyl-β-ionol with an allylic chlorinated derivative carrying an ester functional group. In U.S. Pat. No. 4,035,425, condensation is carried out in the presence of copper and a base. The derivative obtained during this condensation is an acetylenic derivative carrying a hydroxyl or alkoxy unit α to the acetylenic group and carrying an ester group, often an acetate group, in the 15 position, of the following formula:

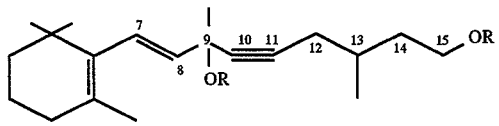

Partial hydrogenation of the acetylenic unit makes it possible to obtain the corresponding ethylenic derivative which, after elimination of the hydroxyl unit or of the alkoxy group situated in the 9 position with the hydrogen in the 12 position (known as 1,4-elimination), makes possible the formation of a double bond which is conjugated with the existing double bond, and which makes it possible to obtain the 11–12 double bond solely in the trans configuration. In U.S. Pat. No. 4,035,425, there is uncertainty regarding the nature of the 9–10 bond. The other bonds, that is to say the 7–8 and 13–14 bonds, are not involved in this conjugation; thus, the vitamin A obtained in U.S. Pat. No. 4,035,425 can only be obtained in the trans form if the ethynyl-β-ionol is trans in the 7–8 position and if the chloroester also has an all-trans bond.

The $C_5$ chloroester of the formula:

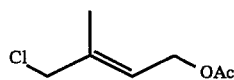

having trans stereochemistry, is a product which is difficult to obtain and, in addition, the double bond has a tendency, during the condensation, to be isomerized to the cis bond. Moreover, the condensation of ethynyl-β-ionol with the $C_5$ chloroester gives, based on the comparative example, infra, an acetylenic derivative in which approximately 20% of the condensation product is an irrecoverable branched by-product of the formula:

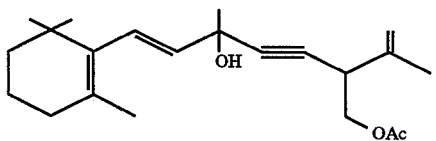

The present invention has made it possible to overcome the disadvantages of the prior art. The present invention makes it possible to start with a $C_5$ halogenated derivative, whether its isomerism is cis or trans, and only causes the production of a limited amount of irrecoverable branched acetylenic isomer.

The present invention is directed to a process for the preparation of an alcohol of formula (I):

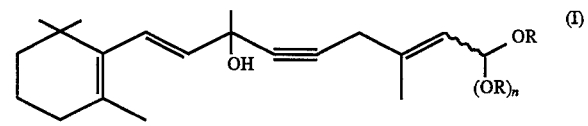

in which n is equal to 0 or 1; wherein when n is 1, R represents an alkyl group having 1 to 4 carbon atoms or both R groups may together represent an alkylidene unit containing 1 to 10 carbon atoms, and when n is 0, R represents a double bond. In other words, the bond connecting the (OR) group to the main chain disappears and becomes hydrogen, and the other remaining R group in the formula forms a double bond between the main chain and the oxygen atom.

The process comprises condensing ethynyl-β-ionol with a chloroacetal of formula (II):

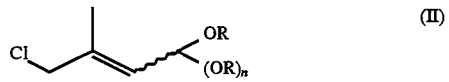

in which n is equal to 0 or 1; wherein when n is 1, R represents an alkyl group having 1 to 4 carbon atoms or both R groups may together represent an alkylidene unit containing 1 to 10 carbon atoms, and when n is 0, R represents a double bond. The same understanding given above for the arrangement of the double bond in formula I also applies here.

A process for the preparation of vitamin A according to the present invention, comprises the steps of:

(a) condensing ethynyl-β-ionol with 1,1-dialkoxy-4-chloro-3-methyl-2-butene in the presence of a catalytically effective amount of a copper-based catalyst and a base;

(b) hydrogenating the condensed compound in the presence of a Lindlar catalyst;

(c) eliminating a hydroxyl group from the hydrogenated compound and hydrolyzing the compound's acetal functional group to obtain retinal; and (d) complexing the retinal with a hydroquinone to correct its isomerism.

The reaction scheme of the first step of a process for the preparation of vitamin A according to the present invention is the following:

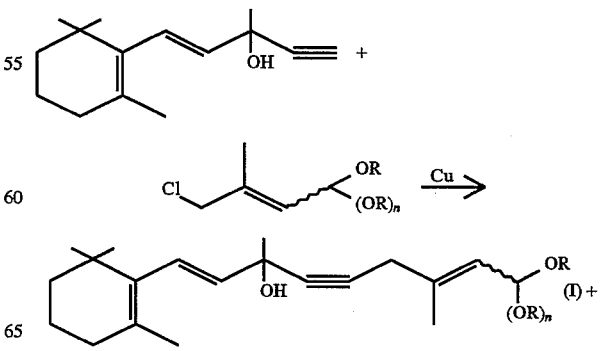

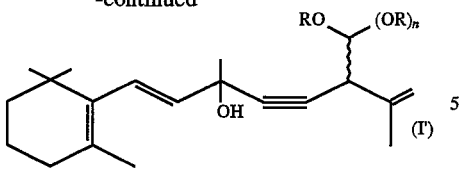

In the above formulae, n is equal to 0 or 1; wherein when n is 1, each R may represent an alkyl group containing 1 to 4 carbon atoms or both R groups may together form an alkylidene group containing 1 to 10 carbon atoms; and when n is 0, R represents a double bond.

The compounds (I) and (I') obtained during this first step are new.

The condensation is carried out in the presence of a copper-based catalyst without prior formation of the condensation compound of the acetylenic compound with the copper.

The copper-based catalyst is preferably chosen from derivatives of copper in the first (I) or second (II) oxidation state such as copper halides, nitrates, alkoxides, cyanide, oxide or thiocyanate. It is more preferable to use copper halides such as cuprous chloride, bromide or iodide.

For better implementation of the present invention, it is preferable to use a cocatalyst based on a monodentate or bidentate phosphine such as tributylphosphine, triphenylphosphine, a tritolylphosphine, a tris-p-methoxyphenylphosphine, a dimethylaminophenylphosphine, 1,2-bis(diphenylphosphino)cyclobutane, 1,4-bis(diphenylphosphino)butane, 1,3-bis(diphenylphosphino)propane, 1,2-bis(diphenylphosphino)ethane or tricyclohexylphosphine, bipyridine, hexamethylphosphoramide, acetylacetone and trisdioxaheptylamine.

The amount of copper introduced for the condensation reaction is a catalytic amount, that is to say that the ratio representing the number of moles of copper to the number of moles of ethynyl-β-ionol ranges from 0.1 to 20% and preferably ranges from 0.5 to 10%. The ratio of the amount used in the prior art is considerably greater than 1 since the stoichiometric organocopper derivative must be prepared prior to bringing into contact with the $C_5$ halogenated ester; the present invention therefore makes possible a significant saving in the amount of catalyst used and avoids the use of magnesium.

The molar ratio of the two reactants brought together, that is the ratio of the $C_5$ chloroacetal to the ethynyl-β-ionol, ranges from 1 to 5 and preferably ranges from 1 to 1.5.

The base used is preferably chosen from alkali metal or alkaline-earth metal acetates, carbonates, phosphates or hydroxides or tertiary amines. It is preferable to use 1 to 5 equivalents of base with respect to the chloroacetal.

A compound of formula (I) obtained after the first step of the process is then hydrogenated according to the following reaction:

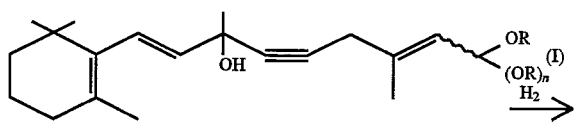

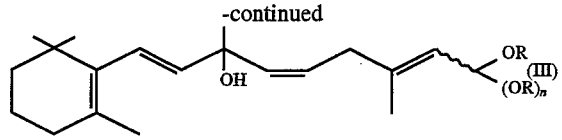

The hydrogenation catalyst may be chosen from poisoned catalysts based on palladium or nickel, also known as Lindlar catalysts. Poisoning can be carried out with lead, an amine such as pyridine, diethylamine or quinoline, or a barium or zinc salt. It is also possible to use an alkali metal iodide as catalyst. It is preferable to use a catalyst deposited on a support chosen from alumina, silica, charcoal or carbon black.

The derivative of formula (III)

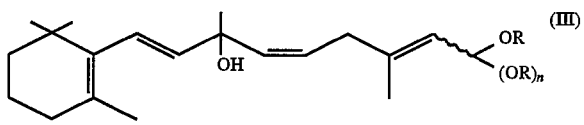

obtained during the second step is also a new compound. The definition for the R group is the same as given for formula I above.

The derivative of formula (III) then undergoes a 1,4-elimination and a deprotection by catalytic action of a strong acid, preferably hydrobromic acid, in an acetone/water medium. Retinal is then obtained which is all-trans over the 7–8, 11–12 bonds but in which the 13–14 bond has the isomerism of the starting $C_5$ compound. This compound is easily corrected by formation of a complex with a hydroquinone, preferably in the presence of iodine, according to the technique described in French Patent No. 1,291,622, the disclosure of which is incorporated herein by reference. French Patent No. 1,291,622 applied successfully to retinal (also known as retinene) discloses the formation of a complex of the trans, trans derivative by means of an isomerization agent that is appropriate to the complexing agent. The formation of a phenol-retinal complex applied to a mixture of retinals makes it possible to isolate, in complex form, 50–60% of the total retinal. The simultaneous isomerization according to this method, caused by a very small quantity of iodine or acid, and with the latter even at ambient temperature, brings about a significant conversion that allows, in favorable cases, isolating 90–100% of the initial retinol in complex form, in a single operation.

The hydroiodic, hydrobromic, hydrochloric, nitric, sulfuric, and p-toluenesulfonic acids bring about this isomerization with varying yields depending upon the quantities and the nature of the acid used.

The phenols that can be used are pyrocatechin and its halogenated derivatives, or hydroquinones, whose crystallized complex with trans-retinal has been described by Eastman-Kodak researchers (French Patent No. 1,098,521 of Feb. 24, 1953). When the complexing agent is pyrocatechin or its halogenated derivatives, iodine is not as favorable as an isomerization agent.

EXAMPLE—(complex with hydroquinone in the presence of iodine)

A quantity of 43.7 g of retinene, value E 380 mμm=892, containing 30% isomers reacting slowly in maleic anhydride is dissolved in 30 cm³ of ether; 50 mg of iodine and 8 g of hydroquinone are added. It is brought to boiling for 15 min and left for one night at +10°. A quantity of 250 cm³ essence is added and it is filtered, resulting in 32.5 g of complex. E 380 mμm=1,152, or an absorption yield of 96%.

After reduction, this raw complex yields a vitamin A alcohol containing only 5% isomers reacting slowly with maleic anhydride.

The use of the acetal functional group makes it possible to both arrive at the retinal and to limit the amount of branched isomer (I').

The present invention will be more completely described using the following examples.

Example 1: Prenylation of ethynyl-β-ionol

|   | | | CuI | K₂CO₃ | dppe |
|---|---|---|---|---|---|
| M | 218 | 164.5 | 190.5 | 138 | 398 |
| m | 50 g | 37.8 g | 4.4 g | 47.4 g | 4.56 g |
| n | 229 mmol | 1 eq | 10% | 1.5 eq | 5% |

Solvent: NMP (100 + 45) ml

Protocol:

$K_2CO_3$ and CuI, as finely ground powders, were successively added, under argon, to a solution of $C_{15}$ (ethynyl-β-ionol) in 100 ml of NMP. The addition of CuI caused an exotherm from 20° to 36° C. After 5 minutes at room temperature, the reaction mixture had turned green. A solution of $C_5$ chloroacetal in 45 ml of NMP and then bisdiphenyl-phosphinoethane were then rapidly added.

The change in the reaction mixture was monitored by liquid chromatography. After 19 hours at room temperature, the reaction mixture (red colour) was poured onto 300 g of ice and extracted with isopropyl ether. The organic phase was then washed with a saturated aqueous NaCl solution, dried over magnesium sulphate, filtered and concentrated. 77.5 g of a viscous reddish oil were obtained, which oil was composed of:

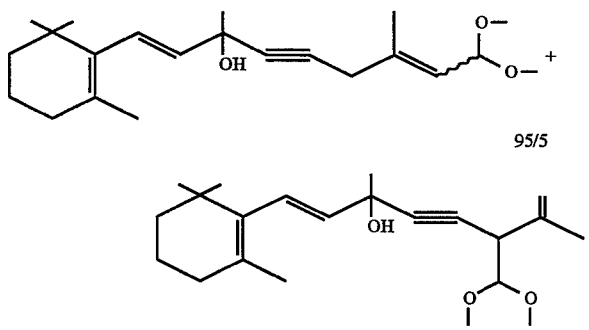

95/5

The yield was 98%. The tests carried out, with modification of the nature of the catalyst and/or of the cocatalyst, are summarized in the following table.

TABLE I

| Solvent | Catalyst (%) and cocatalyst (%) | Ligand (%) | Temperature, time | DC ($C_{15}$) % | $C_{20}$ RY % |
|---|---|---|---|---|---|
| NMP | CuI (10) | dppe (5) | 22° C., 19 h | ≅100 | 98 |
| DMF | CuI (10) | Pφ₃ (20) | 22° C., 24 h 60° C., 5 h | >80 | 66 |
| DMF | CuI (10) | Pφ₃ (20) | 22° C., 20 h | 76 | 68 |
| DMF | CuI (10) | — | 22° C., 24 h | <40 | <40 |
| NMP | CuI (10) | — | 22° C., 37 h | 93 | 69 |
| MeCN | CuI (10) | — | 22° C., 48 h | <30 | <30 |

TABLE I-continued

| Solvent | Catalyst (%) and cocatalyst (%) | Ligand (%) | Temperature, time | DC ($C_{15}$) % | $C_{20}$ RY % |
|---|---|---|---|---|---|
| DMSO | CuI (10) | — | 22° C., 40 h | 84 | 70 |
| Sulpholane | CuI (10) | dppe (5) | 22° C., 48 h | 83 | 84 |
| DMF | CuI (10) Ni(Pφ₃)₄ (5) | — | 22° C., 48 h 60° C., 4 h 30 | <50 | <50 |
| DMF | CuI (10) Pd(Pφ₃)₄ (5) | — | 22° C., 48 h 60° C., 4 h 30 | <50 | <50 |
| DMF | CuI (10) RhCl(Pφ₃)₄ (5) | — | 22° C., 48 h | 76 | 47 |
| NMP | CuCl (10) | Pφ₃ (5) | 22° C., 40 h | 43 | 14 |
| NMP | CuBrMe₂S (5) | Pφ₃ (5) | 22° C., 40 h |  | 25 |
| NMP | CuNO₃(Pφ₃) (10) | — | 22° C., 40 h |  | 25 |
| NMP | CuI (10) | Pφ₃ (5) | 22° C., 40 h | 88 | 79 |
| DMF | CuI (10) | Pφ₃ (5) | 22° C., 36 h | 88 | 79 |
| DMSO | CuI (10) | Pφ₃ (5) | 22° C., 26 h | 90 | 78 |
| DMF | CuI (10) | PCy₃ (5) | 22° C., 36 h | 90 | 76 |
| DMF | CuI (10) | PBu₃ (5) | 22° C., 36 h | 87 | 76 |
| NMP | CuI (10) | dppe (5) | 22° C., 27 h | 90 | 82 |
| NMP | CuI (10) | bipy (5) | 26 h | 88 | 79 |
| NMP | CuI (10) | HMPA (5) | 22° C., 27 h | 76 | 44 |
| NMP | CuI (10) | acac (10) | 22° C., 27 h | 77 | 53 |
| NMP | CuI (10) | TDA₁ (5) | 22° C., 27 h | 75 | 70 |
| NMP | CuI (20) | Pφ₃ (5) | 22° C., 27 h | 84 | 74 |
| NMP | CuI (10) | Pφ₃ (5) | 22° C., 40 h | 88 | 79 |
| NMP | CuI (5) | Pφ₃ (5) | 22° C., 39 h | 88 | 63 |
| NMP | CuI (1) | Pφ₃ (5) | 22° C., 31 h | 60 | 59 |
| NMP/H₂O | CuI (10) | Pφ₃ (5) | 22° C., 24 h | 81 | 55 |
| NMP | CuI (10) | PhSH (5) | 22° C., 24 h | 82 | 60 | dppe: 1,2-bis(diphenylphosphino)ethane
bipy: bipyridine
HMPA: hexamethylphosphoramide
acac: acetylacetone
TDA₁: trisdioxaheptylamine
DC: direct conversion
RY: real yield Example 2: Prenylation of ethynyl-β-ionol

| | | | CuI | K$_2$CO$_3$ | KI |
|---|---|---|---|---|---|
| M | 218 | 164.5 | 190.5 | 138 | 166 |
| m | 500 mg | (376 + 188) mg | 44 | 473 | 380 |
| n | 2.29 mmol | (1 + 0.5) eq | 10% | 1.5 eq | 1 eq |
| | | Solvent: DMF (5 + 2 + 1) ml | | | |

Protocol:

Ethynyl-β-ionol was dissolved in 5 ml of DMF and then KI, K$_2$CO$_3$ and CuI were added under argon.

After 5 min at room temperature, a solution of 1 molar equivalent of C$_5$ in 2 ml of DMF was added dropwise very slowly (approximately 8 h). After a total of 18 h at room temperature, the C$_5$ had completely disappeared. The reaction mixture was then treated with 5 ml of water and then extracted with 2 times 8 ml of ether and the extracts were dried over MgSO$_4$, then filtered and concentrated.

The expected C$_{20}$ was purified by chromatography on silica (eluent: pentane/ether: 75/25). The yield of isolated product was 84%.

E/Z = 89/11

90/10

The procedure used was identical to that described in Example 2. The degree of conversion of ethynyl-β-ionol was 82%. The yield was 75%.

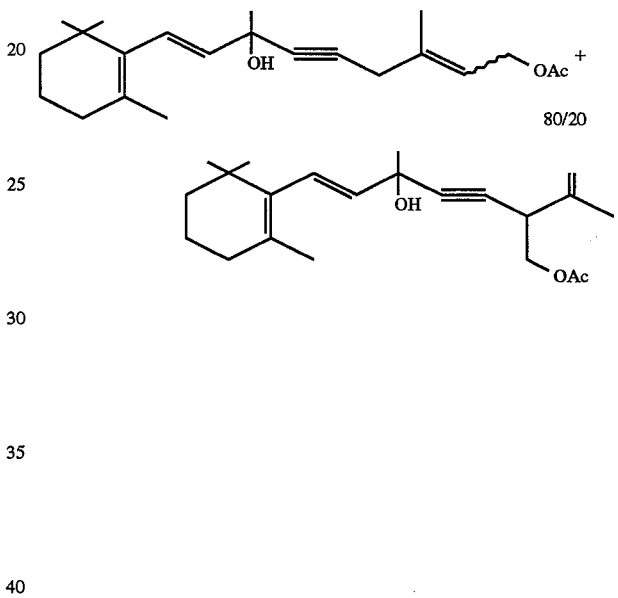

80/20

COMPARATIVE EXAMPLE: Prenylation of ethynl-β-ionol

| | | | CuI | K$_2$CO$_3$ | KI |
|---|---|---|---|---|---|
| M | 218 | 162.5 | 190.5 | 138 | 166 |
| m | 500 mg | 273 mg | 44 mg | 473 mg | 380 mg |
| n | 2.29 mmol | (1 + 0.5) eq | 10% | 1.5 eq | 1 eq |
| | | Solvent: DMF (5 + 2 + 1) ml | | | |

Example 3: Partial hyrogenation of the C<sub>20</sub> hydroxyacetal

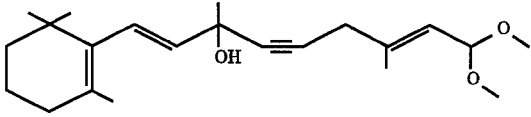

|   |          | 5% Pd on CaCO<sub>3</sub> | Pyridine |
|---|----------|---------------------------|----------|
| M | 346      |                           | 79       |
| m | 854 mg   | 563 mg                    | 10 μl    |
| n | 2.47 mmol| 0.1 eq of Pd<sup>0</sup>  | 5%       |

Solvent: Hexane 42 ml

The catalyst and the pyridine were added successively to a solution of $C_{20}$ in hexane obtained in Example 1 and the mixture was then placed under a hydrogen atmosphere for about 15 hours. The mixture was filtered and then concentrated. The crude yield was 96%.

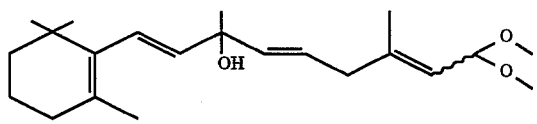

Example 4: Hydrolysis of the hydroxyacetal to retinal

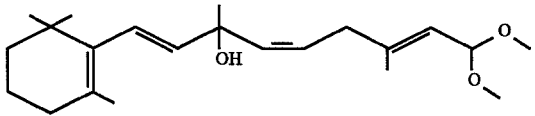

|   |         | HBr | Ionol | H<sub>2</sub>O |
|---|---------|-----|-------|----------------|
| M | 348     |     |       | 18             |
| m | 314 mg  |     | 7 mg  | 190 mg         |
| n | 0.9 mmol| 3%  | 1%    |                |

Solvent: acetone 21 ml

190 μl of water were added to a solution of the $C_{20}$ hydroxyacetal and of ionol and the mixture was then brought to reflux for 5 minutes. 140 μl of a solution composed of 1.5 ml of 48% by weight hydrobromic acid in water and 70.5 ml of acetone was then quickly added.

After 5 minutes at reflux, the starting $C_{20}$ had disappeared. The mixture was then poured onto 20 g of ice and 20 g of water, was then extracted with ether and the extract α dried over MgSO<sub>4</sub>. Retinal was collected with a yield of 73% after chromatography on silica (eluent: pentane/ether: 85/15).

What is claimed is:

1. A process for the preparation of vitamin A, comprising the steps of:
   (a) condensing ethynyl-β-ionol with 1,1-dialkoxy-4-chloro-3-methyl-2-butene in the presence of a catalytically effective amount of a copper-based catalyst and a base;
   (b) hydrogenating the condensed compound in the presence of a Lindlar catalyst;
   (c) eliminating a hydroxyl group from the hydrogenated compound and hydrolyzing the compound's acetal functional group to obtain retinal;
   (d) complexing the retinal with hydroquinone to correct its isomerism to retinol; and
   (e) performing a reduction step on the complexed retinol to obtain vitamin A.

2. A process according to claim 1, wherein the copper-based catalyst is selected from copper halides, nitrates, alkoxides, cyanide, oxide and thiocyanate, and further wherein the copper is in the first (I) or second (II) oxidation state.

3. A process according to claim 2, wherein the copper-based catalyst is selected from copper halides.

4. A process according to claim 3, wherein the copper-based catalyst is cuprous chloride.

5. A process according to claim 1, further comprising a phosphine derivative as a cocatalyst.

6. A process according to claim 1, wherein the catalytic amount of the copper-based catalyst ranges from 0.1 to 20 molar equivalent % with respect to ethynyl-β-ionol.

7. A process according to claim 1, wherein the base is selected from alkali metal or alkaline-earth metal carbonates, acetates, phosphates, tertiary amines, and alkali metal hydroxides.

8. A process according to claim 7, wherein the amount of base ranges from 1 to 5 molar equivalents with respect to the chloroacetal.

9. A process according to claim 1, wherein the hydrogenating step is carried out in the presence of palladium-on-charcoal and in the presence of pyridine.

10. A process according to claim 1, wherein the eliminating step is carried out in the presence of hydrobromic acid in acetone.

11. A process according to claim 1, wherein the complexing step is carried out in the presence of iodine.

12. A process according to claim 1, wherein the molar ratio of the 1,1-dialkoxy-4-chloro-3-methyl-2-butene to the ethynyl-β-ionol ranges from 1 to 5.

13. A process according to claim 12, wherein the molar ratio ranges from 1 to 1.5.

14. A process according to claim 6, wherein the catalytic amount of the copper-based catalyst ranges from 0.5 to 10 molar equivalent % with respect to ethynyl-β-ionol.

* * * * *